United States Patent [19]

Matson et al.

[11] Patent Number: 4,602,114

[45] Date of Patent: Jul. 22, 1986

[54] PREPARATION OF ε-CAPROLACTONE

[75] Inventors: Michael S. Matson; Gerald R. Kahle, both of Bartlesville, Okla.

[73] Assignee: Phillips Petroleum Company, Bartlesville, Okla.

[21] Appl. No.: 621,986

[22] Filed: Jun. 18, 1984

[51] Int. Cl.$^4$ .......................................... C07D 313/04
[52] U.S. Cl. ............................................... 549/266
[58] Field of Search ........................................ 549/266

[56] References Cited

U.S. PATENT DOCUMENTS

| | | | |
|---|---|---|---|
| 3,061,614 | 10/1962 | Sweeney et al. | 260/343.6 |
| 3,700,706 | 10/1972 | Butter | 260/410.9 R |
| 3,859,319 | 1/1975 | Mrowca | 260/410.6 |
| 3,919,272 | 11/1975 | Knifton | 260/410.9 R |
| 3,952,020 | 4/1976 | Stapp | 260/343.6 |

OTHER PUBLICATIONS

J. Org. Chem., vol. 41, No. 17, pp. 2885–2990 (1976) Knifton.
Preprints, Div. of Petroleum Chemistry, Inc., Symposium on Homogenous Catalysis, American Chemical Society, Houston, Tex., Mar. 23–28, 1980, pp. 368–371.
*Carbon Monoxide in Organic Synthesis* by Jürgen Falbe, Translated by C. R. Adams (1970), pp. 157–159.

*Primary Examiner*—Jane T. Fan
*Attorney, Agent, or Firm*—French and Doescher

[57] ABSTRACT

A process for the production of ε-caprolactone wherein 4-penten-1-ol is reacted carbon monoxide in the presence of a ligand-stabilized Pd(II) catalyst complexed with a Group IVB metal halide.

20 Claims, No Drawings

PREPARATION OF ε-CAPROLACTONE

The invention relates generally to the preparation of lactones. In one aspect the invention relates to the preparation of caprolactones. More particularly, but not by way of limitation, the invention relates to a process for preparing ε-caprolactone by the carbonylation of 4-penten-1-ol.

Lactones, for example, caprolactones, are useful in perfumery and can be used in the masking of odors in many kinds of compositions. They are particularly valuable as chemical intermediates, reacting with alcohols to form esters, with ammonia to form amides, and with other bases, halogen acids and so forth. The esters thus formed are useful as softeners and plasticizers for polymeric materials.

It is an object of the present invention to provide a novel process for the preparation of caprolactones.

Another object of the present invention is to provide a novel process for the preparation of ε-caprolactone.

Yet another object of the present invention is to provide a process for the preparation of ε-caprolactone which is simple and economical.

Other objects, aspects and advantages of the present invention will be apparent to those skilled in the art from a reading of the specification and appended claims.

In accordance with this invention, it has been discovered that ε-caprolactones are prepared by the reaction of 4-penten-1-ol with carbon monoxide in the presence of a platinum group metal compound as catalyst. A suitable catalyst for use in the process of the present invention is a ligand-stabilized palladium(II) catalyst complexed with a Group IVB metal halide.

U.S. Pat. No. 3,700,706 discloses the use of tin cocatalysts with palladium catalysts of the formula $L_mPdX_y$ wherein L is an organophosphine and X is an acid function, e.g. halide, in the carbonylation of olefinic hydrocarbons. The products of the reaction can be esters if an alcohol is present or carboxylic acids if water is present. This patent does not disclose the use of alkenols in the carbonylation reaction.

U.S. Pat. No. 3,919,272 and *The Journal of Organic Chemistry*, Vol. 41, No. 17, pp. 2885-2990 (1976) disclose the use of ligand-stabilized palladium(II) catalysts complexed with a Group IVB metal halide, e.g. Sn or Ge halides, for the carbonylation of olefinic hydrocarbons to produce esters or acids as described in the first-mentioned patent. These last-mentioned references also fail to disclose the use of alkenols in the carbonylation reaction.

U.S. Pat. No. 3,859,319 discloses that olefinically unsaturated alcohols (alkenols) can be carbonylated with a palladium compound having bridging phosphido groups and optionally promoted with halogen compounds of tin. However, it will be noted that the products of the disclosed carbonylation reaction are said to be polyesters.

The book *Carbon Monoxide in Organic Synthesis* by Jürgen Falbe, translated by C. R. Adams (1970), pages 157-159 discloses the reaction of unsaturated primary alcohols with carbon monoxide to give lactones. Side reactions such as isomerization and dehydration of the starting material are emphasized. Palladium catalyst systems are not disclosed, nor is the production of ε-caprolactone from 4-penten-1-ol. Furthermore, acetonitrile or its derivatives are said to improve selectivity toward the lactone in the disclosed process.

Preprints, The Division of Petroleum Chemistry, Inc., Symposium on Homogenous Catalysis, American Chemical Society, Houston, Tex., Mar. 23-28, 1980, pp. 368-371, entitled "Scope of the Pd-Catalyzed Cyclocarbonylation of Unsaturated Alcohols to α-Substituted Lactones" by Jack R. Norton, discloses the cyclocarbonylation of unsaturated alcohols to α-substituted lactones with a palladium/tin (catalyst/cocatalyst) system. The conversion of 3-buten-1-ol to α-methyl-γ-butyrolactone is shown, but the reaction of 4-penten-1-ol is not shown. Furthermore, acetonitrile is disclosed as the apparently preferred solvent.

In view of the above disclosures of the relevant art, our discovery that ε-caprolactone could be obtained in significant yields by the cyclocarbonylation of 4-penten-1-ol in the presence of the ligand-stabilized palladium(II) catalyst complexed with a Group IVB metal halide is highly surprising. It is further surprising that acetonitrile has been proved to be ineffective as a solvent for this reaction.

The use of ligand-stabilized palladium(II) catayst systems complexed with a Group IVB metal halide is essential to the inventive carbonylation process. The key elements of the ligands used to stabilize the palladium(II) catalysts are selected from those elements of Group VB or VIB of the Periodic Chart of the Elements selected from nitrogen, arsenic, antimony, sulfur, selenium, bismuth and phosphorous. Illustrative ligands used to stabilize the palladium(II) catalysts are:

$As(C_6H_5)_3$,
$Sb(C_6H_5)_3$,
$Bl(C_6H_5)_3$,
$P(C_6H_5)_3$,
$P(CH_3)_2(C_6H_5)$,
$As(n-C_4H_9)_3$,
$P(p-CH_3C_6H_4)_3$,
$P(C_6H_{11})_3$,
$(C_6H_5)_2P(CH_2)_2P(C_6H_5)_2$,
$P(OC_6H_5)_3$,
$S(C_6H_5)_2$,
$P[(p-CH_3C_6H_4)(C_6H_5)_2]$, pyridine, ethylenediamine and 1,10-phenanthroline.

Illustrative of the Group IVB metal halides that can be complexed with the ligand-stabilized palladium(II) to form an active carbonylation catalyst are tin(II) chloride, tin(IV) chloride, tin(II) bromide, germanium(II) chloride and germanium(II) bromide.

The following complexes are among the many ligand-stabilized palladium(II)-Group IVB metal halide complexes which can be used in the inventive carbonylation as the catalyst system:

$PdCl_2[P(C_6H_5)_3]_2$-$SnCl_2$,
$PdCl_2[As(C_6H_5)_3]_2$-$SnCl_2$,
$PdBr_2[P(C_5H_6)_3]_2$-$SnBr_2$,
$PdBr_2[Sb(C_6H_5)_3]_2$-$GeBr_2$,
$PdCl_2[P(C_6H_5)_3]_2$-$GeCl_2$,
$PdCl_2[P(C_2H_5)_2$-$(C_6H_5)]_2$-$SnCl_2$,
$PdCl_2[P(p-CH_3C_6H_4)_3]_2$-$SnCl_2$,
$PdCl_2[C_6H_5)_2PCH_2CH_2P(C_6H_5)_2]$-$SnCl_2$,
$PdCl_2[As(CH_3)_2C_6H_5]_2$-$SnCl_2$, and
$PdCl_2[P(C_6H_{11})_3]_2$-$SnCl_2$.

One convenient mode of preparation of the ligand-stabilized palladium(II)-Group IVB metal halide catalyst complexes is in situ wherein palladium(II) halide complex such as $PdCl_2[P(C_6H_5)_3]_2$ is mixed with a large molar excess of Group IVB metal halide, preferentially $SnCl_2$ or $GeCl_2$.

While the molar ratio of stannous chloride to the ligand-stabilized palladium(II) halide is not critical, generally a ratio of from 1 to 8 moles of stannous chloride for each mole of palladium(II) complex provides good results, more preferably a ratio of from 3 to 6 moles of stannous chloride for each mole of palladium-(II) complex is desired.

In the process of the present invention, 4-penten-1-ol is converted to ε-caprolactone in significant amounts in a cyclocarbonylation reaction utilizing the catalyst system described above. 4-Penten-1-ol is a known compound and is commercially available.

Solvents employed in the process of this invention are preferably selected from aliphatic and cyclic ketones having from 3-12 carbon atoms per molecule, and mixtures of any two or more thereof. Hydrocarbons, e.g., paraffin, cycloparaffin and aromatic, of from 5-12 carbon atoms per molecule, and mixtures of any two or more thereof, are also suitable although somewhat less preferred since the catalyst, reactants, and products tend to be less soluble in the hydrocarbons than in the ketones. Examples of suitable solvents include, but are not limited to, acetone, methyl ethyl ketone, methyl isobutyl ketone, cyclopentanone, cyclohexanone, cyclododecanone, pentane, hexane, cyclohexane, benzene, toluene, dodecane and the like, as well as mixtures of any two or more thereof.

The concentration of 4-penten-1-ol in the reaction mixture of the process of the present invention is generally in the range from about 1 to about 30 weight percent, more preferably in the range from about 10 to about 20 weight percent based on the total weight of the reaction mixture.

The amount of catalyst employed in the process of the present invention is conveniently expressed in terms of weight percent Pd metal based on the weight of the 4-penten-1-ol feed. Generally, this weight percent Pd metal can range from about 0.1 to about 10, but preferably the weight percent Pd metal ranges from about 0.5 to about 2.

In the cyclocarbonylation reaction of the process of the present invention, carbon monoxide must be present in at least one mole for each mole of 4-penten-1-ol reactant. In actual practice it is convenient to employ a significant excess of CO, and to monitor the progress of the reaction by observing the decrease in CO pressure and then optionally adding CO from time to time to bring the pressure back up to the initial process pressure. The reaction is thus considered to be essentially complete when the CO pressure does not fall over a reasonable period of time. CO pressures in the practice of the process of the present invention can range generally from about 500 psig to about 4,000 psig, more preferably from 2,000 psig to about 4,000 psig, and more preferably still from about 2,000 psig to about 3,000 psig.

The reaction temperature for the cyclocarbonylation process of the invention can be any temperature at which the desired reaction proceeds satisfactorily, however, satisfactory reaction temperatures range from about 50° to about 130° C., and more preferably from 75° to about 120° C.

Under the reaction conditions described above, the cyclocarbonylation process of the present invention is usually complete within a period from about 0.5 to about 5 hours. As noted earlier, the reaction can be allowed to continue until there is essentially no further uptake of CO as indicated by no further decrease in CO pressure over the reaction mixture.

The process of the present invention can be conducted in conventional reactors suitable for the CO pressures and temperatures contemplated. The reactors should be equipped with suitable conventional mixing means to facilitate mixing of the vapor and liquid phases in the reaction sysem.

At the conclusion of the reaction period in the process of the present invention, the resulting product mixture is cooled to near ambient temperature, the excess CO is safely vented and the product mixture is filtered or decanted from any solids that may be present. The product mixture can then be generally subjected to a fractional distillation in order to recover ε-caprolactone from the product mixture which usually comprises at least one other lactone including geometrical isomers thereof. The complexity of the reaction mixture will depend to a great extent on the purity of the feed material, 4-penten-1-ol, employed.

The ε-caprolactone product of the process of the present invention is a well known chemical of commercial importance. For example, in addition to those uses set forth above, it can be polymerized to a polyester which is a useful intermediate for the production of polyurethanes for coatings, sealants and the like.

The caprolactone product of the process of the present invention can be alternately characterized by the formula

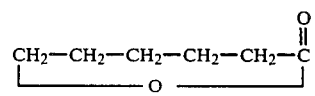

In the following examples illustrative of the present invention, the reactions were conducted in a 300 cc Magnadrive autoclave made of Inconel and equipped with stirring and heating means.

The reagents were used without further purification or treatment.

The general reaction procedure involved adding the solids (Sn and/or Pd components) to the open autoclave under a $N_2$ purge stream. Solvent and feed were added next and the reactor closed. After a brief $N_2$ purge, the reactor was then purged several times with low pressure CO (about 200 psig). The mixture was heated with stirring to the desired temperature under an initial CO pressure of about 2,400 psig and then allowed to react for about 3 hours. The mixture was cooled to about 25° C. and then vented to atmospheric pressure. The reactor contents were then withdrawn to a glass flask and sampled by gas/liquid chromatography using a 10 foot column of OV225 silicone polymer (3% by weight) on Chromosorb P support with 30 cc/min helium carrier gas over a range of from about 50° C. (4 min hold to about 225° C. (15 min hold) at a heating rate of about 15° /min. A thermal conductivity detector was employed in this system. Samples were also generally analyzed by gas chromatography/mass spectrometry combined instrumentation.

In the examples that follow the symbol $P\phi_3$ represents the triphenyl phosphine ligand $P(C_6H_5)_3$.

EXAMPLE 1

The autoclave was charged with 0.58 g (0.83 mmole) $PdCl_2(P\phi_3)_2$, 0.76 g (4.0 mmole) $SnCl_2$, 100.05 g acetonitrile solvent and 14.94 g (173 mmole) of 4-penten-1-ol.

The reaction mixture was pressured to 2,364 psig with CO and the temperature raised from 23° C. to 100° C. during 1.5 hours then held at that temperature for another hour, cooled to 23° C. (2,138 psig) and vented. Although the pressure differential at 23° C. indicated some consumption of CO there was no indication in the gas chromatography analysis that ε-caprolactone or any other analogous lactone had been formed.

This result was surprising in view of the teachings of the prior art that acetonitrile is a preferred solvent in cyclocarbonylation reactions.

EXAMPLE 2

In another control run allyl alcohol, 16.26 g (280 mmole), was reacted in methyl isobutyl ketone (MIBK) solvent, 100.08 g, with CO in presence of 0.58 g (0.83 mmole) $PdCl_2(P\phi_3)_2$ and 0.72 g (3.8 mmole) $SnCl_2$ catalyst. The reactor was pressured to 2,400 psig with CO at 21° C. then heated to 100° C. over 1.5 hours and held at 100° C. for 6.5 hours, cooled and vented. Since the CO pressure remained unchanged after reaching 100° C. it was assumed that little if any reaction took place. Furthermore, gas chromatographic analysis of the final reaction mixture showed little if any change in the allyl alcohol concentration from the original mixture.

The non-reactivity of allyl alcohol under the conditions employed is again surprising in view of the prior art teaching.

EXAMPLE 3

A series of cyclocarbonylation runs was made using 4-penten-1-ol reactant in methyl isobutyl ketone (MIBK) solvent with the $PdCl_2(P\phi_3)_2/SnCl_2$ catalyst system. The details of these runs and the results obtained are presented in Tables I and II below. Except as noted these runs were made at 100° C. for 3 hours.

TABLE I

| Run No. | Feed,[a] g(mmole) | MIBK, g | Pd,[b] g(mmole) | $SnCl_2$, g(mmole) | Conv., % | Lactones Yield[c] |
|---|---|---|---|---|---|---|
| 1 | 15.4(179) | 99.5 | 0.56(0.80) | 0.72(3.8) | 100 | 75-80 |
| 2 | 14.9(173) | 100.7 | 0.58(0.83) | 0.74(3.9) | 100 | 80-90 |
| 3[d] | 15.4(179) | 99.5 | 0.56(0.80) | 0.75(3.9) | 100 | 75 |
| 4 | 15.3(178) | 99.6 | 0.56(0.80) | 0 | No reaction | |
| 5 | 15.1(175) | 100.5 | 0.56(0.80) | 1.44(7.6) | No reaction | |

[a]4-penten-1-ol
[b]as $PdCl_2(P\phi_3)_2$
[c]Based on gas chromatography analysis it appears that 3 lactones are produced. See Table II.
[d]Run at 75° C.

TABLE II

| Run No. | Lactones Yield[a] | Mole Ratio of ε-Caprolactone to Other Products[b] |
|---|---|---|
| 1 | 75-80 | 3.22 |
| 2 | 80-90 | 3.20 |
| 3 | 75 | 3.44 |

[a]See footnote (c) of Table I
[b]From gas chromatography peak ratios. The first peak eluting after solvent and residual feed (including impurities) is believed to be a substituted butyrolactone. The second peak appears to be the expected isomer of ε-caprolactone, i.e. 2-methyl-5-hydroxypentanoic acid lactone, arising from CO addition at the No. 4 carbon instead of the No. 5 carbon. The third peak was confirmed by GC-Mass Spectral Analysis as ε-caprolactone.

The results for Runs 1-3 in Tables I and II show that significant yields of ε-caprolactone can be obtained by the cyclocarbonylation of 4-penten-1-ol in methyl isobutyl ketone with a $PdCl_2(P\phi_3)_2/SnCl_2$ catalyst system. However, Run 4 shows that the Sn component is necessary for the system to be active yet if too much Sn is present (Run 5) the system is again essentially inactive. The mole ratio of Sn to Pd was 9.5 in this run. In Runs 1-3 the mole ratio of Sn to Pd was 4.8, 4.7, and 4.9 respectively.

EXAMPLE 4

Two additional runs were conducted in which 4-penten-1-ol was subjected to cyclocarbonylation reaction conditions employing the $PdCl_2(P\phi_3)_2/SnCl_2$ catalyst system in MIBK solvent (99-100 g) according to the instant invention. Both runs employed 0.56 g (0.80 mmole) $PdCl_2(P\phi_3)_2$ and 0.77 g (4.1 mmole) $SnCl_2$ in the catalyst composition. Reaction time for each run was 3 hours. The mixtures were analyzed by gas chromatography using a capillary column system. The details of these runs and the results obtained are presented in Table III below.

TABLE III

| Run No. | Feed,[a] g(mmole) | CO,[b] psig | Temp., °C. | Conv., % | Lactone Yield |
|---|---|---|---|---|---|
| 6 | 11.24(130) | 2,000 | 100-118 | >95 | [c] |
| 7 | 10.96(127) | 750 | 100-120 | >95 | [d] |

[a]4-penten-1-ol
[b]Initial CO pressure
[c]about 44% yield of ε-caprolactone and about 23% yield of α-methylvalerolactone. Balance appeared to heavies of unknown structure.
[d]About 23% yield of ε-caprolactone and 15% of α-methylvalerolactone. Balance appeared to be heavies of unknown structure.

The results illustrated in Table III show improved lactone selectivity at higher initial CO pressures.

EXAMPLE 5

In another control run 4-penten-2-ol was subjected to the cyclocarbonylation reaction conditions employed in the instant invention. The autoclave was charged with 0.51 g (0.75 mmole) $PdCl_2(P\phi_3)_2$, 0.69 g (3.6 mmole) $SnCl_2$, 86.1 g methyl isobutyl ketone (MIBK) and 10.0 g (116 mmole) of 4-penten-2-ol. After the usual flushing with $N_2$ and then with CO, the reactor was pressured to 2,419 psig with CO at 23° C. The temperature was raised to 100° C. over 0.5 hour then held at 100° C. for 2.5 hours. The reactor was cooled to 23° C. (2,213 psig) and vented to atmospheric pressure. The reaction mixture was analyzed by gas chromatography and gas chromatography/mass spectrum combination. Three principal peaks appeared to include two dimethyl butyrolactone isomers and a 6-membered lactone with a methyl substituent. No evidence of ε-caprolactone production was observed. Possible impurities in the 4-penten-2-ol were believed to contribute to the complexity of the reaction mixture.

In summary, the data herein disclosed reveal a novel process for the production of ε-caprolactone by means of the catalytic carbonylation of 4-penten-1-ol.

Reasonable variations and modifications which will become apparent to those skilled in the art can be made in this invention without departing from the spirit and scope thereof.

We claim:

1. A process for the preparation of ε-caprolactone which comprises:
   (a) reacting 4-penten-1-ol with CO in the presence of a ligand-stabilized Pd(II) catalyst complexed with a Group IVB metal halide and in the absence of acetonitrile to produce ε-caprolactone in the resulting product mixture; and (b) recovering ε-caprolactone from the product mixture.

2. A process in accordance with claim 1 wherein said catalyst is characterized further as having a mole ratio of the Group IVB metal halide to the Pd component in the range from about 1 to about 8.

3. A process in accordance with the claim 1 wherein said catalyst is characterized further as having a mole ratio of the Group IVB metal halide to the Pd component in the range from about 3 to about 6.

4. A process in accordance with claim 1 wherein step (a) is performed in the presence of a solvent.

5. A process in accordance with claim 1 wherein step (a) is performed in the presence of a solvent selected from the group consisting of aliphatic and cyclic ketones having from 3 to 12 carbon atoms per molecule, and paraffin, cycloparaffin and aromatic hydrocarbons having from 5 to 12 carbon atoms per molecule, and mixtures of any two or more thereof.

6. A process in accordance with claim 1 wherein step (a) is performed in the presence of a solvent selected from the group consisting of aliphatic and cyclic ketones and mixtures of any two more thereof.

7. A process in accordance with claim 1 wherein step (a) is performed in the presence of a solvent selected from the group consisting of aliphatic and cyclic ketones, and paraffin, cycloparaffin and aromatic hydrocarbons, and mixtures of any two or more thereof.

8. A process in accordance with claim 1 wherein step (a) is performed in the presence of a solvent selected from the group consisting of aliphatic and cyclic ketones having from 3 to 12 carbon atoms per molecule and mixtures of any two or more thereof.

9. A process in accordance with claim 1 wherein step (a) is performed in the presence of a solvent, and wherein the concentration of 4-penten-1-ol in the reaction mixture is in the range from about 1 to about 30 weight percent based on the total weight of the 4-penten-1-ol, CO, solvent and catalysts comprising the reaction mixture.

10. A process in accordance with claim 1 wherein step (a) is performed in the presence of a solvent, and wherein the concentration of 4-penten-1-ol in the reaction mixture is in the range from about 10 to about 20 weight percent based on the total weight of the 4-penten-1-ol, CO, solvent and catalyst comprising the reaction mixture.

11. A process in accordance with claim 1 wherein step (b) is characterized further to include fractionally distilling the product mixture to recover ε-caprolactone therefrom.

12. A process in accordance with claim 1 wherein step (a) is performed with excess CO at a pressure in the range from about 500 to about 4000 psig, at a temperature in the range from about 50° C. to about 130° C., and until there is substantially no further uptake of CO in the reaction mixture.

13. A process in accordance with claim 1 wherein said catalyst comprises $PdCl_2[P(C_6H_5)_3]_2$ complexed with $SnCl_2$.

14. A process in accordance with claim 1 wherein the catalyst is employed in step (a) in an amount based on the weight percent Pd metal in the catalyst based on the total weight of the 4-penten-1-ol in the reaction mixture, said weight percent Pd metal being in the range from about 0.1 to about 10.

15. A process in accordance with claim 1 wherein the catalyst is employed in step (a) in an amount based on the weight percent Pd metal in the catalyst based on the total weight of the 4-penten-1-ol in the reaction mixture, said weight percent Pd metal being in the range from about 0.5 to about 2.

16. A process in accordance with claim 1 wherein the pressure in step (a) is in the range from about 500 psig to about 4000 psig.

17. A process for the preparation of a caprolactone having the formula

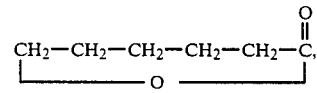

comprising:
(a) reacting 4-penten-1-ol with CO in the presence of a ligand-stabilized Pd(II) catalyst complexed with a Group IVB metal halide and in the absence of acetonitrile to produce a caprolatone having said formula in the resulting product mixture; and
(b) recovering said thus produced caprolactone from the product mixture.

18. A process in accordance with claim 17 wherein said catalyst comprises $PdCl_2[P(C_6H_5)_3]_2$ complexed with $SnCl_2$.

19. A process in accordance with claim 17 wherein said catalyst is characterized further as having a mole ratio of the Group IVB metal halide to the Pd component in the range from about 1 to about 8.

20. A process in accordance with claim 17 wherein step (a) is performed in the presence of a solvent selected from the group consisting of aliphatic and cyclic ketones having from 3 to 12 carbon atoms per molecule, and paraffin, cycloparaffin and aromatic hydrocarbons having from 5 to 12 carbon atoms per molecule, and mixtures of any two or more thereof.

* * * * *